United States Patent [19]

Horng

[11] Patent Number: 4,931,654
[45] Date of Patent: Jun. 5, 1990

[54] RADIANT AIR-STERILIZING APPARATUS

[76] Inventor: Wen-Jenn Horng, No. 28, Alley 1, Ta-Ho I Lane, Ta-Ho-Li, Hsi-Tun Dist., Taichung City, Taiwan

[21] Appl. No.: 423,030

[22] Filed: Oct. 18, 1989

[51] Int. Cl.$^5$ .............................................. A61L 9/20
[52] U.S. Cl. ................................... 250/436; 250/435; 250/432 R; 250/428; 250/504 R; 422/24
[58] Field of Search .................. 250/436, 435, 432 R, 250/428, 504 R; 422/24

[56] References Cited

U.S. PATENT DOCUMENTS

| | | | |
|---|---|---|---|
| 2,354,817 | 8/1944 | Law | 422/24 |
| 2,413,704 | 1/1947 | Glatthar et al. | 422/24 |
| 2,553,711 | 5/1951 | Jackson | 422/24 |
| 2,855,641 | 10/1958 | Stein | 250/436 |
| 3,433,949 | 3/1969 | Truhan | 250/504 R |
| 3,674,421 | 12/1969 | Decupper | 422/24 |
| 3,745,750 | 7/1973 | Arff | 422/24 |
| 3,750,370 | 8/1973 | Brauss et al. | 422/24 |
| 3,844,741 | 10/1974 | Dimitrik | 250/504 R |
| 3,937,967 | 2/1976 | Steinitz | 250/436 |
| 3,967,927 | 7/1976 | Patterson | 250/432 R |
| 4,210,429 | 7/1980 | Golstein | 422/24 |
| 4,297,583 | 10/1981 | Nerod | 250/504 R |
| 4,469,951 | 9/1984 | Coco et al. | 250/504 R |
| 4,806,768 | 2/1989 | Keutenedjian | 250/436 |

Primary Examiner—Janice A. Howell
Assistant Examiner—Kiet T. Nguyen
Attorney, Agent, or Firm—Ladas & Parry

[57] ABSTRACT

An air sterilizing apparatus includes an enclosed housing which accommodates radiant sterilizing tubes carried by a holder capable of moving out of the housing or retracting thereinto by means of a moving mechanism. When the holder is moved out, the radiant sterilizing tubes thus exposed sterilize the external air surrounding the housing. When the holder is moved back into the housing, the radiant sterilizing tubes sterilize the air drawn into the enclosed housing through an inlet, after which the sterilized air is discharged through an outlet of the housing.

10 Claims, 6 Drawing Sheets

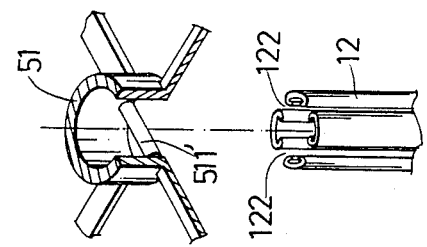
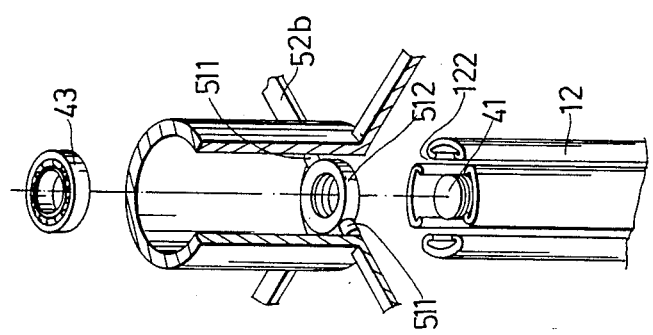
FIG.4A
FIG.3A

RADIANT AIR-STERILIZING APPARATUS

BACKGROUND OF THE INVENTION

This invention relates to an air sterilizing apparatus and a radiant sterilizing apparatus which employs radiant tubes in an enclosed housing arranged to sterilize the air drawn into the housing.

According to a survey reported in a U.S. medical magazine, 5% of the total patients in all U.S. hospitals were the victims of "hospital contracted infection," because these 5% patients caught infections in the hospitals after being admitted in. Consequently, hospital treatment for those 5% patients were unnecessarily prolonged. Statistically, about 50 thousand out of those 5% were estimated to have died of the "hospital contracted infection" every year. As a result, "hospital contracted infection" ranks "sixth" among the ten vital causes of mortality. Hospitals in other areas having inferior facilities than those of the United States, face a more serious problem of said "hospital contracted infection," so that most people are reluctant to go for hospital treatment and hospitalization, particularly for their children whose immune systems are weak. However, hospitals are unable to take remedial measures since every patient in the hospitals is deemed either a virus or a bacteria carrier, readily spreading the virus or bacteria existing in their upper respiratory organ through their breathing, talking, coughing and sneezing, and go as far as infecting even the medical personnel with undermined immunological defenses. In order to improve this situation, a conventional ultraviolet-ray sterilizing apparatus has been produced for use in a public building. However, since ultraviolet radiation is harmful to human body, said ultraviolet-ray sterilizing apparatus cannot be used safely in a hospital building unless all the patients and medical personnel first evacuated from the place to be sterilized, thereby causing a considerable inconvenience, inasmuch as the patients and medical personnel have to stay in their respective places in the hospital building. Thus, radiation from said ultraviolet-ray sterilizing apparatus could inflict a serious injury when exposed to the patients and medical personnel.

SUMMARY OF THE INVENTION

It is accordingly a primary object of the present invention to provide an air sterilizing and filtering apparatus which completely destroys bacteria and microbes existing in the air of the place associated with said apparatus without causing injury to the persons staying in said place.

It is another object of the present invention to provide an air sterilizing and filtering apparatus with a heating element by which heating and radiation can be alternatively effected to make the bacteria and microbes therein to become inactive and unstable by the warm temperature therein so as to achieve and an utmost bactericidal effect therewith.

According to the present invention, an air sterilizing apparatus comprises: an enclosed housing having a first end wall provided with an outlet hole, the housing further having an air inlet opening means and an air outlet opening means; a fan provided in the enclosed housing adjacent to the air inlet opening means; a radiant sterilizing means provided in the enclosed housing; means for holding the radiant sterilizing means, the holding means being movable between a first position in which the radiant sterilizing means is enclosed in the enclosed housing and a second position in which the radiant sterilizing means extends outward from the enclosed housing through the outlet hole, the holding means incorporating a cover means which closes the outlet hole when in the first position of the holding means; means for moving the holding means, connected to the holding means; and means for guiding the holding means to move outward and inward through the outlet hole. The apparatus may further comprise a heating means provided in the enclosed housing adjacent to the air inlet opening means. Advantageously, a filter means may be provided at the air inlet and outlet opening means.

In one aspect of the invention, the enclosed housing is provided with an inner support plate near a second end wall of the enclosed housing opposite to the first end wall, the guiding means including elongated guide plates which extend from the first end wall adjacent to the outlet hole to the inner support plate.

The holding means may include an elongated hollow body which is slideably sleeved on the guide plates. and a plurality of pairs of holding arms extending radially from two opposite ends of the hollow body.

The radiant sterilizing means may include a plurality of radiant sterilizing tubes each held by one of the pairs of the holding arms.

The moving means may include a motor, a transmission belt connected to said motor and said hollow body, and a pulley associated with said transmission belt. Alternatively, the moving means may include a rotary hydraulic actuator, an operating screw rod connected to the rotary hydraulic actuator and extending within the guide plates, and means for engaging the screw rod and the hollow body.

The present exemplary preferred embodiment will be described in detail with reference to the accompanying drawings, in which;

BRIEF DESCRIPTION OF THE DRAWINGS

FIG. 3A is a fragmentary view of the first embodiment;

FIG. 4A is a sectional view of the second embodiment;

DETAILED DESCRIPTION OF THE PREFERRED EMBODIMENT

Figure 1:
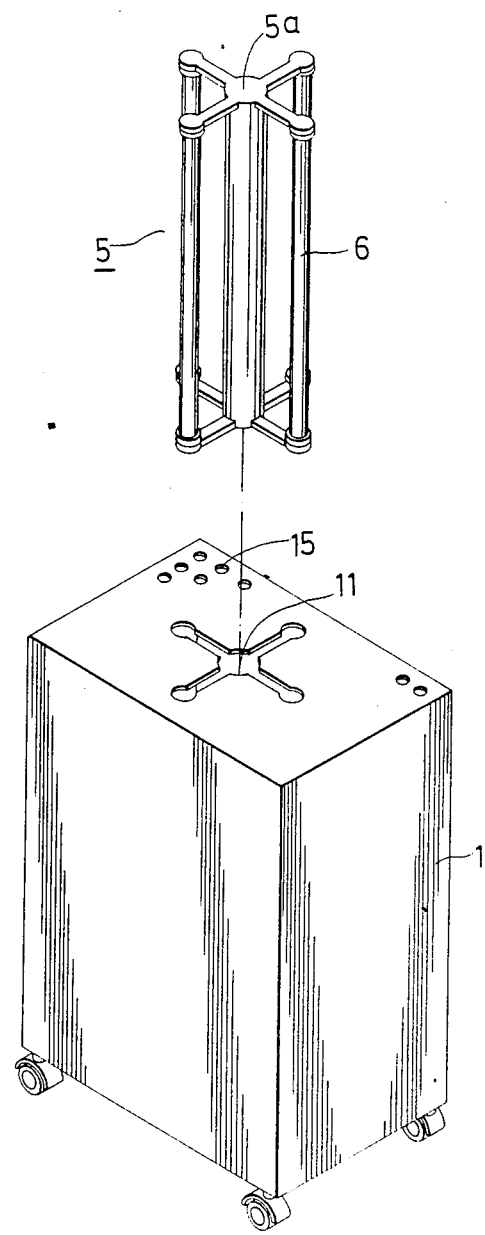
FIG. 1 shows an exploded view of a first embodiment of an air sterilizing apparatus according to the present invention.
Figure 2:
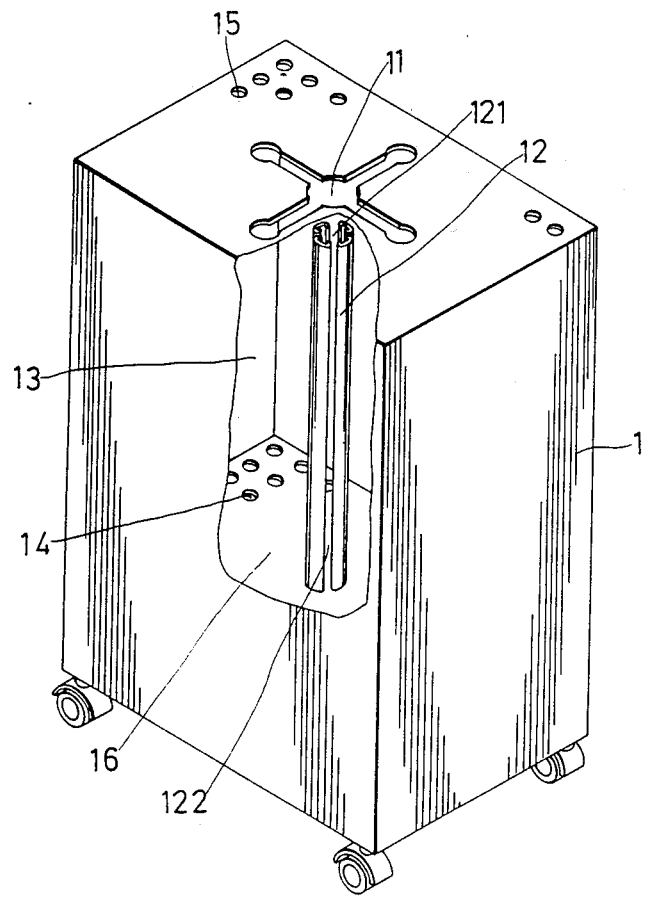
FIG. 2 is a partially sectioned perspective view of the air sterilizing apparatus of FIG. 1.
Figure 3:
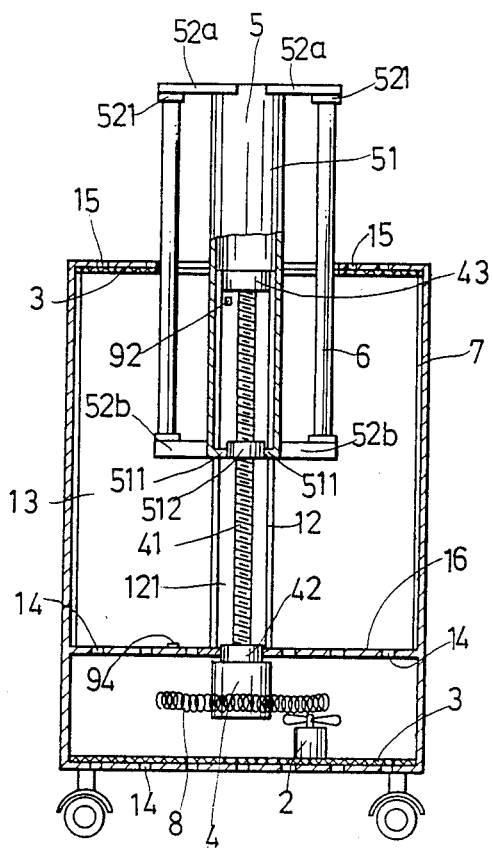
FIG. 3 is a sectional view of the air sterilizing apparatus of FIG. 1.

The drawings illustrating the embodiments of the present invention are provided with like numerals for like elements.

Referring to FIGS. 1 to 4, a sterilizing apparatus according to the present invention is shown, having an enclosed housing 1, a fan 2, two filter members 3, a rotary hydraulic actuator 4, a holding means or carriage 5, radiant sterilizing elements 6 and reflectors 7.

The enclosed housing 1 is provided with an outlet hole 11 at a top wall thereof. An inner support plate 16 is provided adjacent to the bottom wall of the housing 1, dividing the housing 1 into upper and lower compartments. Four elongated guide plates 12 of curved cross-section extend between the support plate 16 and the top wall of the housing 1 and are spaced apart annularly, confining a space for receiving an operating screw rod 41 which will be described hereinafter. Air inlet openings 14 are provided in the bottom wall, and the support plate 16 and air outlet openings 15 are provided in the top wall of the enclosed housing 1, The fan 2 is mounted on the bottom wall of housing 1 adjacent to the air inlet openings 14 for the purpose of drawing air into the enclosed housing 1.

The filters or screen elements 3 are attached to the top and bottom wall of the housing 1 near the inlet and outlet openings 14, 15 for the purpose of filtering dust and reducing the rate of air entering the housing 1.

The rotary hydraulic actuator 4 is mounted to the support plate 16 in the lower chamber of the housing 1. A screw rod 41 is provided in the space confined by the guide plates 12. The screw rod 41 is journalled in the support plate 16 by means of a bearing assembly 42 and the lower end thereof is connected to the rotary hydraulic actuator 4. An upper bearing 43 is attached to the upper ends of the guide plates 12 adjacent to the outlet hole 11 of the top wall, holding the upper end of the screw rod 41.

The carriage 5 includes a hollow body 51 which is sleeved around the guide plates 12. The lower end of the hollow body 51 has four flanges 511 which extend inward through the spaces between the guide plates 12 and are connected to a sleeve member 512 which is sleeved around and engaged with the screw rod 41. Four pairs of upper and lower arms 52a, 52b extend radially outward from the opposite ends of the hollow body 51, each holding a lamp holder 521. The upper ends of the carriage 5 is provided with a cover 5a to cover the hole 11 when the carriage 5 is entirely retracted in the housing 1.

The carriage 5 can be moved upward and downward by the screw rod 41 when the screw rod 41 is rotated by the hydraulic actuator 4. Accordingly, the light tubes 6 can extend outward from the housing 1.

The radiant sterilizing elements 6 are in the form of light tubes each of which are held by a pair of lamp holders 521.

Reflectors 7 are provided on the inner side of the wall of the enclosed housing 1 so as to reflect the rays emitted from the radiant sterilizing elements 6.

A heating element 8 is provided in the enclosed housing 1 below the support plate 16 for the purpose of heating air drawn into the housing 1.

Micro switches 94 are respectively attached to the upper portion of the guide plates 12 and the partition plate to control the movement of the carriage 5. During the moving operation of the carriage 5, the carriage 5 will touch the upper or lower micro switch 94 which in turn stops the operation of the hydraulic actuator 4. The system that controls the operation of hydraulic actuator is an electrically operated type. This control system will not be detailed in this application since it does not form any part of the present invention.

The light or radiant tubes 6 emit ultraviolet rays which are well known as that producing a sterilizing radiant energy. The wavelength of the emitted rays employed in the radiant tubes 6 is 2537 Å.

During use, the apparatus of the present invention can be placed in two positions, in other words, the radiant tubes 6 can be exposed from or enclosed in the enclosed housing 1 when the apparatus is used. When the radiant tubes 6 are exposed, they emit visible ultraviolet rays into the surrounding air and provide a direct sterilizing effect to the space surrounding the apparatus. In this case, no person may be in the room or the space surrounding the apparatus. When the radiant tubes 6 are retracted in the housing 1, the ultraviolet rays emitted from the tubes 6 sterilize the air drawn into the enclosed housing 1. In this case, the sterilizing rays are isolated within the apparatus so that no harm will come to the persons in the surrounding area.

If it is desired to withdraw the radiant tubes 6 from the enclosed housing 1, one may actuate the hydraulic actuator 4 which operates the screw rod 41, thereby moving outward the carriage 5. When the radiant tubes 6 are in their retracted positions, the surrounding air is drawn into the enclosed housing 1 through the inlet openings 14 and the filter 3. The heating element 8 which is disposed upstream of the radiant sterilizing tubes 6 generates heat and pre-treat the admitted air or provide the admitted air with a degree of sterilizing effect. The heated air is effectively sterilized when passing through the chamber of the radiant sterilizing elements 6 and finally escapes from the apparatus of the present invention. In addition to the heating element 8, the apparatus of the present invention can be provided with a cooling unit (not shown) in the chamber 13 of the housing 1. The cooling unit also provide a sterilizing effect.

Figure 4:
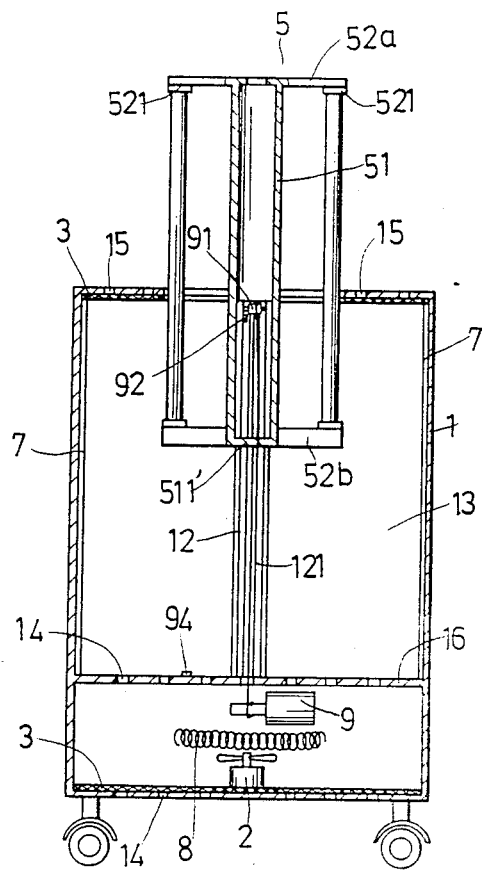
FIG. 4 is a sectional view of a second embodiment of the present invention.

FIG. 4 shows a second embodiment of the sterilizing apparatus which differs from the first embodiment in that the second embodiment includes a motor 9 as a power means, and a pulley 91 and a transmission belt 92 to transmit movement to the carriage 5, in place of the hydraulic actuator 4 and screw rod 41 of the first embodiment. One end of the transmission belt 92 is connected to the output of the motor 9. The other end of the transmission belt 92 passes over the pulley and is connected to the hollow body 51. Referring to FIG. 4A, the lower end of the hollow body 51 is provided with a diametral cross member 511' for the connection with the transmission belt 92.

Figure 5:
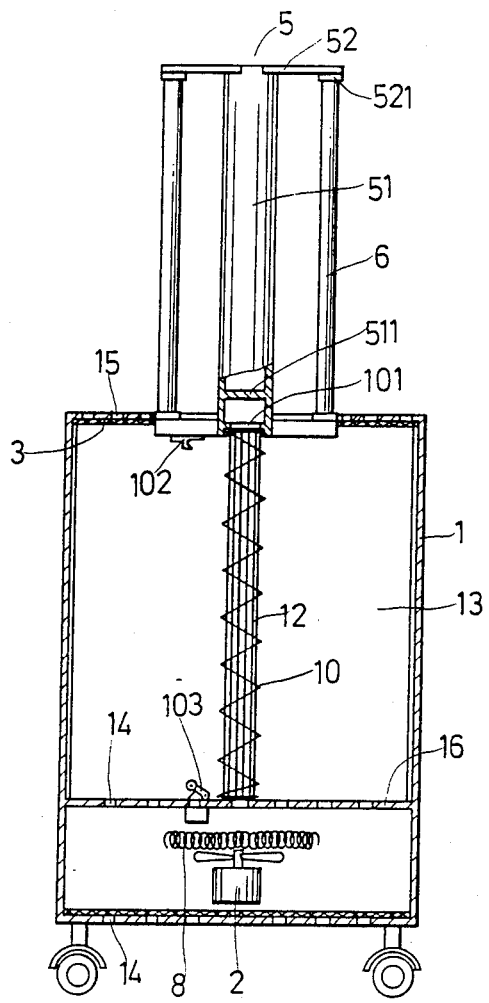
FIG. 5 is a sectional view of a third embodiment of the present invention.

FIG. 5 shows a third embodiment of the invention which differs from the previous embodiments in that neither the hydraulic actuator 4 nor the motor 9 is provided. Instead, this embodiment includes a compression spring 10 which is provided around the guide plates 12 between the support plate 16 and an end flange 101 of the hollow body 51. Accordingly, the carriage 5 is biased to extend outward from the enclosed housing 1 by the force of the spring 10. When the carriage 5 is pressed into the enclosed housing 1 against the force of the spring 10, the carriage 5 is held in the housing 1 by the engagement of a hook element 102 attached to the bottom of the carriage 5 and a catch member 103 attached to the support plate 16, thereby being prevented from extending outward. The hook element 102 and the catch member 103 are of the type which can alternatively interengage and disengage from one another when the carriage 5 is depressed successively. This type of engaging member is known and will not be detailed herein.

With the invention thus explained, it is apparent that various modifications and variations can be made without departing from the scope of the invention. It is therefore intended that the invention be limited as indicated in the appended claims.

What I claim is:

1. An air sterilizing apparatus comprising:
an enclosed housing having a first end wall provided with an outlet hole, said housing further having an air inlet opening means and an air outlet opening means,
a fan provided in the enclosed housing adjacent to said air inlet opening means;
a radiant sterilizing means provided in said enclosed housing;
means for holding said radiant sterilizing means, said holding means being movable between a first position in which said radiant sterilizing means is enclosed in said enclosed housing and a second position in which said radiant sterilizing means extends outward from said enclosed housing through said outlet hole, said holding means incorporating a cover means which closes said outlet hole when said holding means in the first position;
means for moving said holding means, connected to said holding means; and
means for guiding said holding means to move outward and inward through said outlet hole.

2. An air sterilizing apparatus as claimed in claim 1, further comprising a heating means provided in said enclosed housing adjacent to said air inlet opening means.

3. An air sterilizing apparatus as claimed in claim 1, further comprising filter means provided at said air inlet and outlet opening means.

4. An air sterilizing apparatus as claimed in claim 1, wherein said enclosed housing is provided with an inner support plate near a second end wall of said enclosed housing opposite to said first end wall, said guiding means including elongated guide plates which extend from said first end wall adjacent said outlet hole, to said inner support plate.

5. An air sterilizing apparatus as claimed in claim 4, wherein said holding means includes an elongated hollow body which is slideably sleeved on said guide plates and a plurality of pairs of holding arms extending radially from two opposite ends of said hollow body.

6. An air sterilizing apparatus as claimed in claim 5, wherein said radiant sterilizing means includes a plurality of radiant sterilizing tubes each held by each pair of said holding arms.

7. An air sterilizing apparatus as claimed in claim 6, wherein said moving means includes a motor, a transmission belt connected to said motor and said hollow body, and a pulley associated with said transmission belt.

8. An air sterilizing apparatus as claimed in claim 6, wherein said moving means includes a rotary hydraulic actuator, an operating screw rod connected to said rotary hydraulic actuator and extending within said guide plates, and means for engaging said screw rod and said hollow body.

9. An air sterilizing apparatus as claimed in claim 6, wherein said moving means includes a compression spring provided around said guide plates to bias said hollow body to move outward.

10. An air sterilizing apparatus as claimed in claim 9, further including means for catching said hollow body so as to prevent said hollow body from moving outward when said hollow body is retracted, by depression, into said enclosed housing.

* * * * *